United States Patent
Umebayashi (10) Patent No.: US 10,130,522 B2
(45) Date of Patent: Nov. 20, 2018

(54) MANUFACTURING METHOD FOR DISPOSABLE WORN ARTICLE

(71) Applicant: ZUIKO CORPORATION, Osaka (JP)

(72) Inventor: Toyoshi Umebayashi, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 190 days.

(21) Appl. No.: 15/108,863

(22) PCT Filed: Jan. 28, 2015

(86) PCT No.: PCT/JP2015/052315
§ 371 (c)(1),
(2) Date: Jun. 29, 2016

(87) PCT Pub. No.: WO2015/115462
PCT Pub. Date: Aug. 6, 2015

(65) Prior Publication Data
US 2016/0324694 A1    Nov. 10, 2016

(30) Foreign Application Priority Data
Feb. 3, 2014 (JP) .................. 2014-018235

(51) Int. Cl.
*A61F 13/15* (2006.01)
*A61F 13/49* (2006.01)
(Continued)

(52) U.S. Cl.
CPC .. *A61F 13/15593* (2013.01); *A61F 13/15699* (2013.01); *A61F 13/49012* (2013.01);
(Continued)

(58) Field of Classification Search
CPC .................. A61F 13/15593; B29C 65/74
See application file for complete search history.

(56) References Cited

U.S. PATENT DOCUMENTS 5,246,433 A * 9/1993 Hasse ............. A61F 13/49009
604/358
5,713,884 A * 2/1998 Osborn, III ....... A61F 13/47218
604/373
(Continued)

FOREIGN PATENT DOCUMENTS

EP        1719484 A1 * 11/2006 ........ A61F 13/15723
JP     2005-279077 A    10/2005
(Continued)

OTHER PUBLICATIONS

International Search Report for corresponding International Application No. PCT/JP2015/052315 dated Apr. 21, 2015.

*Primary Examiner* — Christopher T Schatz
(74) *Attorney, Agent, or Firm* — Renner, Otto, Boisselle & Sklar, LLP (57) ABSTRACT

A method for manufacturing a disposable worn article including the steps of: carrying a continuous sheet (W1) continuous in a carrying direction (X1); placing elastic members (F3), continuous in the carrying direction of the continuous sheet, on the continuous sheet with the continuous elastic members stretched; placing discontinuous sheets (W2), each of which has a predetermined length, on the continuous sheet intermittently and successively in the carrying direction so that the continuous elastic members are sandwiched between the discontinuous sheets and the continuous sheet; and carrying out a first joining step in which, in an area where each of the discontinuous sheets is placed, the continuous sheet, each of the discontinuous sheets, and the continuous elastic members are joined to one another, intermittently in the carrying direction, along first joining portions (32A, 32C) extending in a width direction (Y) crossing the carrying direction.

2 Claims, 9 Drawing Sheets

(51) Int. Cl.
*B29C 65/74* (2006.01)
*B29L 9/00* (2006.01)
*B29L 31/48* (2006.01)

(52) U.S. Cl.
CPC ......... *B29C 65/74* (2013.01); *B29L 2009/001* (2013.01); *B29L 2031/4878* (2013.01)

(56) References Cited

U.S. PATENT DOCUMENTS

2004/0035521 A1* 2/2004 Nakakado ......... A61F 13/15593 156/229
2006/0151093 A1* 7/2006 Nakakado ......... A61F 13/15593 156/164

FOREIGN PATENT DOCUMENTS

JP         2013-116196     6/2013
WO   WO 2013/080852 A1    6/2013

* cited by examiner

MANUFACTURING METHOD FOR DISPOSABLE WORN ARTICLE

TECHNICAL FIELD

The present invention relates to methods for manufacturing worn articles such as disposable pants and diapers.

BACKGROUND ART

As an exterior portion covering the torso of the wearer, a worn article structure is employed in which elastic threads are sandwiched between two sheets (the first patent document). The aforementioned exterior portion of the worn article is formed so that discontinuous sheets (sheet pieces) are intermittently placed on the continuous sheet, and thread-like elastic members are sandwiched between the discontinuous sheets and the continuous sheet (the second patent document).

CITATION LIST

Patent Literature

[First Patent Document] JP 2005-279077 A (Abstract)
[Second Patent Document] WO13/080852 A (Abstract)

SUMMARY OF INVENTION

In general, adhesive is continuously applied in a longitudinal direction on an area where discontinuous sheets are to be placed when a continuous sheet, discontinuous sheets, and elastic members are joined together. In this case, texture (feeling of a fabric) of the exterior portion will deteriorate. Furthermore, when adhesive agent is used for joining, a lot of adhesive agent will be necessary.

Thus, an object of the present invention is to provide a method for manufacturing a disposable article, the method giving the article good texture and being less likely to waste adhesive when adhesive is used for bonding.

A method for manufacturing a disposable worn article according to the present invention including the steps of:

carrying a continuous sheet that is continuous in a carrying direction;

placing a plurality of continuous elastic members, which are continuous in the carrying direction of the continuous sheet, on the continuous sheet with each of the continuous elastic members stretched;

placing a plurality of discontinuous (non-continuous) sheets, each of which has a predetermined length, on the continuous sheet intermittently and successively in the carrying direction so that the continuous elastic members are sandwiched between the discontinuous sheets and the continuous sheet; and carrying out a first joining (bonding) step in which, in an area where each of the discontinuous sheets is placed, the continuous sheet, each of the discontinuous sheets, and the continuous elastic members are joined (bonded) to one another along a plurality of first joining (bonding) portions extending in a width direction crossing the carrying direction, with the joining performed intermittently in the carrying direction.

In the present invention, the first joining portions are intermittently provided, with the three types of elements (continuous sheet, discontinuous sheets, and elastic members) being joined together in the first joining portions. That is, the three types of elements are not joined on the entire surface of each of the discontinuous sheets. Therefore, the texture (feeling of a fabric) of the laminate will improve.

BRIEF DESCRIPTION OF DRAWINGS

FIGS. 1A, 1B, and 1C show each Embodiment 1 of a worn article of the present invention, wherein

FIGS. 4A, 4B, and 4C show each Embodiment 2 of a worn article of the present invention, wherein

FIGS. 6A, 6B, and 6C show each Embodiment 3 of a worn article of the present invention, wherein

FIGS. 8A, 8B, and 8C show each Embodiment 4 of a worn article of the present invention, wherein

Note that FIGS. 1A, 3A, 3B, 4A, 5A, 5B, 6A, 7A, 7B, 8A, 9A, and 9B show each an exploded perspective view in which sheets and non-woven fabrics are shifted from one another in the top-bottom direction of the drawing sheet so that it is easy to see how these members are laid on one another.

DESCRIPTION OF EMBODIMENTS

Preferably, the present invention further includes the step of:

cutting the continuous elastic members between two discontinuous sheets of the plurality of discontinuous sheets, the two discontinuous sheets being adjacent to each other in the carrying direction In this case, contraction force of the elastic members is not exerted in the part between the discontinuous sheets. Additionally, the cut elastic members shrink and shorten toward the discontinuous sheets by so-called "snap-back effect." Thus, an appearance of the part between the discontinuous sheets will be improved.

Preferably, in the first joining step, the first joining portions are formed in opposite end portions of each of the discontinuous sheets in the carrying direction and in a central portion of each of the discontinuous sheets, the central portion being spaced apart from the opposite end portions and between the opposite end portions.

In this case, each discontinuous sheet is stably secured to the continuous sheet in its entire length in the carrying direction.

More preferably, the present invention further includes the step of:

successively placing one end portion, in a longitudinal direction, of each of absorbent bodies absorbing body fluid on the continuous sheet between two discontinuous sheets of the plurality of discontinuous sheets, the two discontinuous sheets being adjacent to each other in the carrying direction.

In this case, the end portion of the absorbent body is laminated on a part of the continuous sheet where the discontinuous sheets are not placed. Thus, the wearer will be less likely to feel stiffness in the end portions of the absorbent body when he/she wears the worn article such as a diaper. Additionally, a moderate (reasonable) stiffness will be applied on a thin continuous sheet. Furthermore, when a design (pattern) or the like is printed on a non-skin-contact surface side (the side not facing a skin of the wearer when a worn article is worn) of the absorbent body, the print will be clearly visible via the continuous sheet.

More preferably, the present invention further includes the step of:

cutting the continuous sheet and each of the discontinuous sheets in the central portion along the width direction crossing (perpendicular to) the carrying direction in order to obtain individual worn articles.

In this case, two side panels are formed from one discontinuous sheet.

Preferably, in the first joining step, the continuous sheet, each of the discontinuous sheets, and the continuous elastic members are joined to one another by an adhesive to thereby intermittently form the first joining portions.

In this case, the adhesive is intermittently applied in the carrying direction on, for example, the continuous sheet. Thus, it is less likely to waste the adhesive.

The present invention further includes the step of:

carrying out a second joining (bonding) step in which, between the plurality of first joining portions in the area, the continuous sheet and each of the discontinuous sheets are intermittently joined (bonded) to each other on a plurality of second joining (bonding) portions, with the joining performed along a stretching direction of the elastic members.

In this case, the continuous sheet and the discontinuous sheet are joined in the stretching direction of the elastic member as well, stabilizing a joint (bonding) state of both sheets.

More preferably, the second joining step is carried out so that the plurality of second joining portions are formed between two continuous elastic members of the continuous elastic members, the two continuous elastic members being adjacent to each other in the width direction.

In this case, it is likely to keep the arrangement of the elastic members adjacent to each other in a desired state.

More preferably, the second joining step is carried out so that the plurality of second joining portions are formed along edges of each of the discontinuous sheets, the edges being opposite in the width direction.

In this case, a joint (bonding) state of the continuous sheet and the discontinuous sheet will be stabilized, and the elastic members will be unlikely to protrude from the side edges.

The present invention will be understood more clearly from the following description of preferred embodiments taken in conjunction with the accompanying drawings. However, the embodiments and the drawings are merely illustrative, and shall not be relied upon for the purpose of defining the scope of the present invention. The scope of the present invention shall be defined only by the appended claims. In the accompanying drawings, like reference numerals denote like components throughout the plurality of figures.

EMBODIMENTS

Embodiment 1

A structure of a worn article 1 according to Embodiment 1 of the present invention will now be described with reference to the drawings.

Figure 1A:
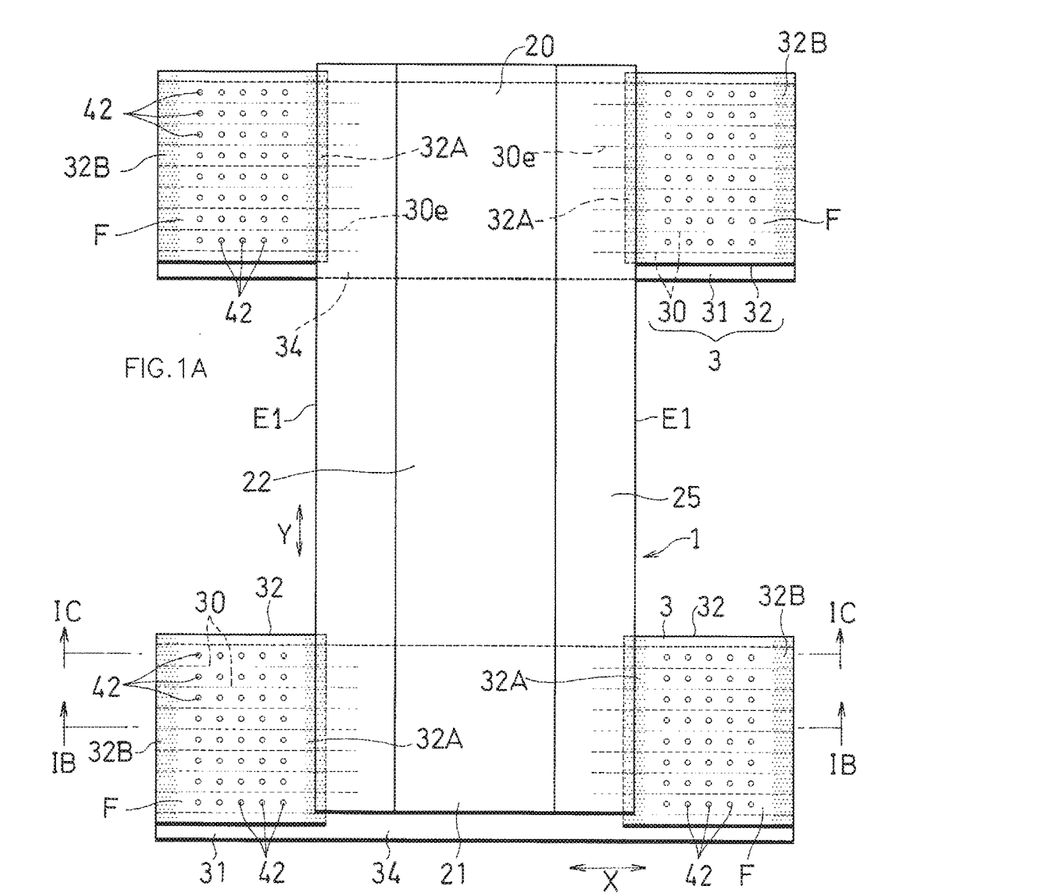
FIG. 1A is a schematic exploded perspective view showing the article unfolded as seen in a diagonally forward direction.
Figure 1B:
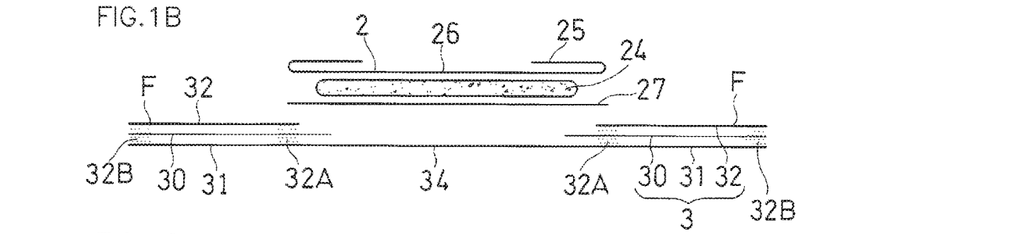
FIGS. 1B and 1C show respectively a cross-sectional view along IB-IB of FIG. 1A and a cross-sectional view along IC-IC of FIG. 1A.
Figure 1C:
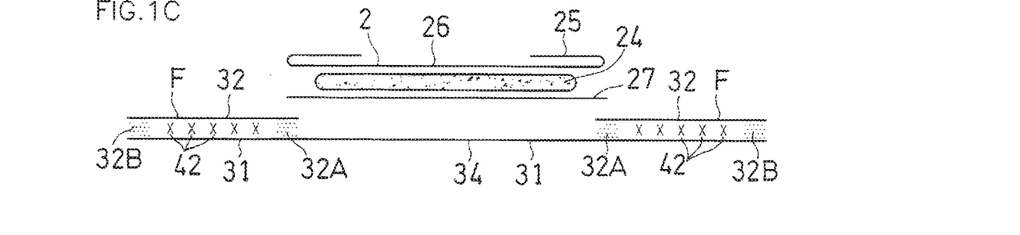
Figure 2:
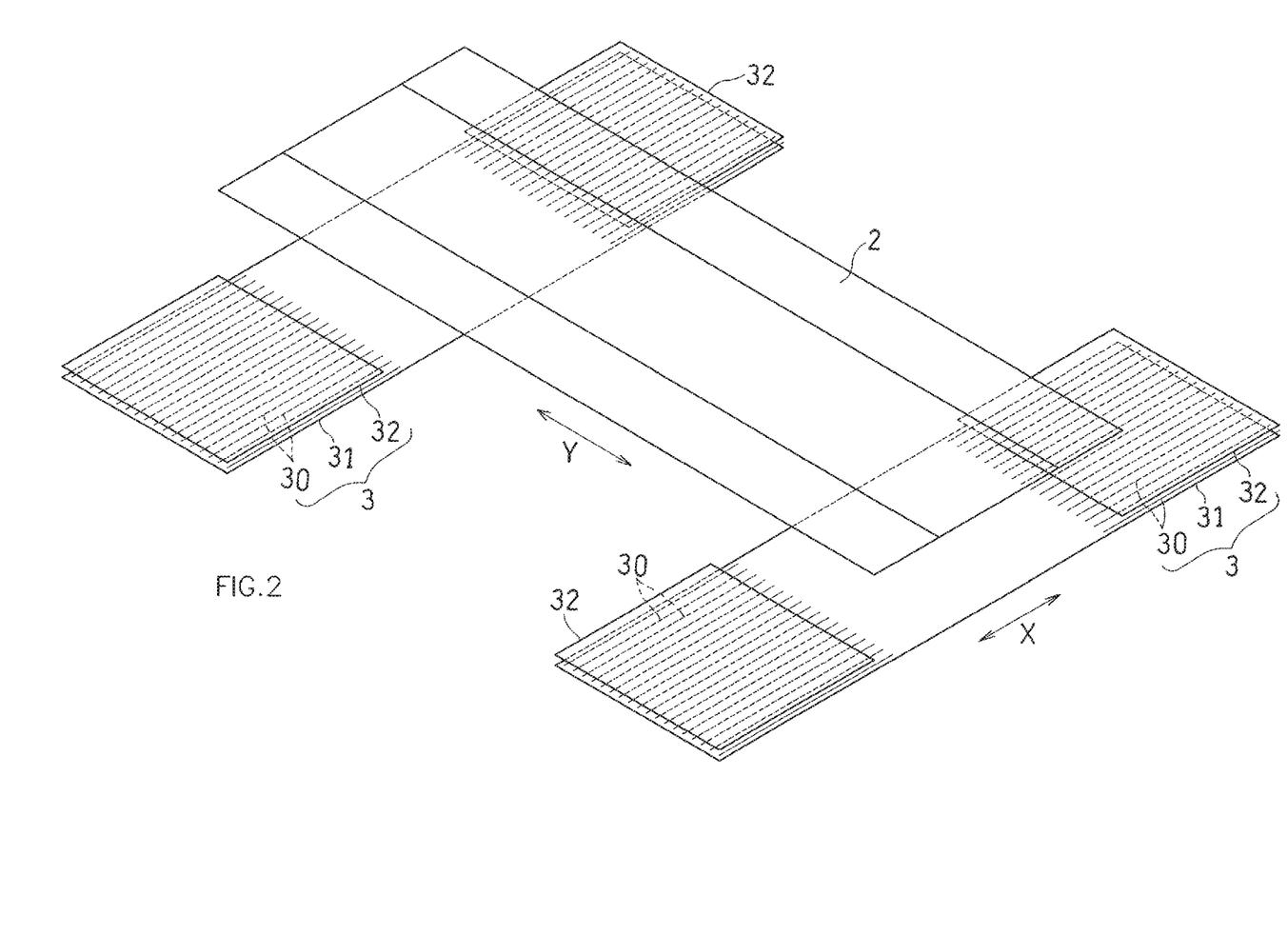
FIG. 2 is a schematic exploded perspective view showing a worn article.
Figure 3A:
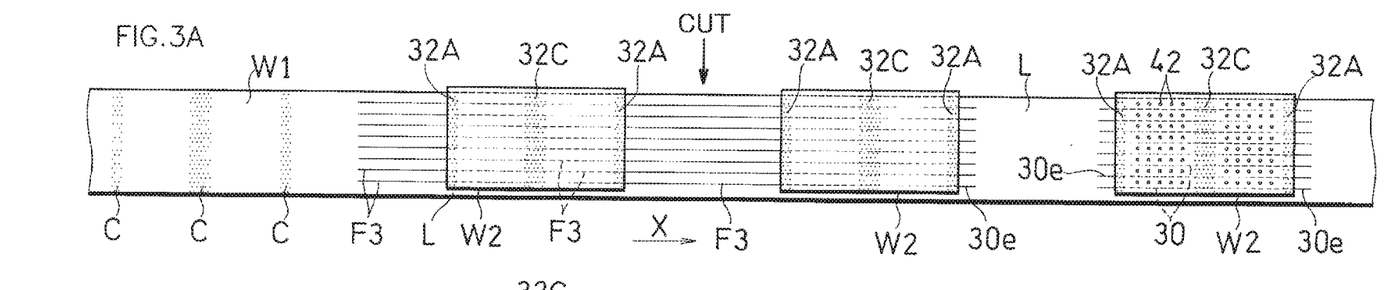
FIGS. 3A and 3B are each a schematic exploded perspective view showing an example of a method for manufacturing the worn article.
Figure 3B:
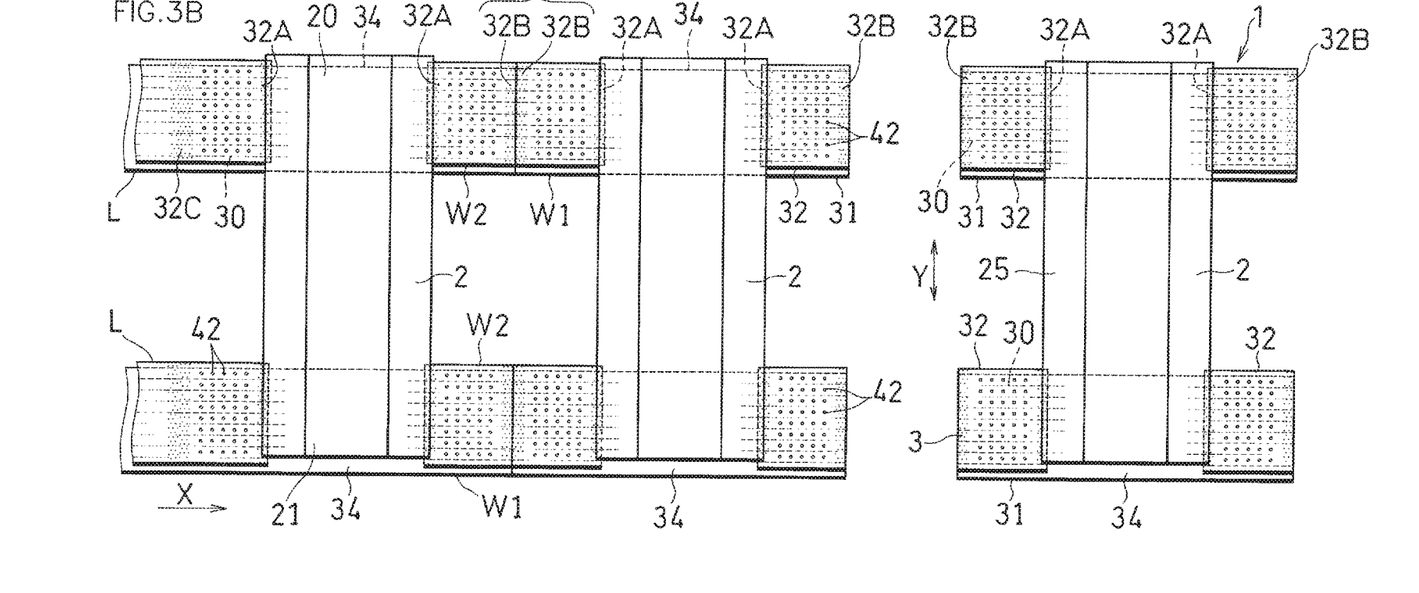

FIGS. 1 to 3 show Embodiment 1.

As shown in FIGS. 1A and 1B, the worn article 1 of Embodiment 1 includes an absorbent body (an example of an interior portion) 2, and a pair of (front and back) around-torso members 3 and 3 (an example of an exterior portion). The absorbent body 2 includes a front portion 20, a back portion 21, and a crotch portion 22. The front portion 20 extends in the girth direction X covering the front torso (the front portion of the torso) of the wearer. The back portion 21 extends in the girth direction X covering the back torso (the back portion of the torso) of the wearer. The crotch portion 22 covers the crotch of the wearer between the front portion 20 and the back portion 21.

The crotch portion 22 is continuous with the front portion 20 and the back portion 21, and extends in the length (longitudinal) direction Y perpendicular (crossing at right angles with) to the girth direction X. The absorbent body 2 forms a part or whole of the crotch portion 22.

In FIG. 1A, the present worn article is worn while the crotch portion 22 is folded in two along a virtual line parallel to the girth direction X. Thus, end portions in the girth direction X of the front around-torso member 3 and those of the back around-torso member 3 are laid on each other.

As shown in FIG. 1B, an absorbent core 24 is provided in the absorbent body 2. The absorbent core 24 absorbs body fluids. The absorbent core 24 is sandwiched between a top sheet 26 and a back sheet 27. The sheets 26 and 27 and the absorbent core 24 are layered on one another.

In FIG. 1B, the top sheet 26 is made of a thin non-woven fabric having a liquid permeability, and covers the skin-contact surface of the absorbent core 24. A cuff 25 may be provided on this top sheet 26. The top sheet 26 is made of an essentially non-stretchable non-woven fabric.

In the present invention, the "skin-contact surface" refers to an inner surface that directly or indirectly contacts the skin of the wearer when the diaper is worn, and it directly or indirectly opposes (faces) the skin of the wearer.

The back sheet 27 covers the non-skin-contact surface of the absorbent core 24, and is made of a liquid-impermeable resin sheet. An exterior non-woven fabric (not shown) may be bonded to and layered on the non-skin-contact surface of the back sheet 27. The resin sheet and the exterior non-woven fabric are essentially non-stretchable.

In the present invention, the "non-skin-contact surface" refers to an outer surface, opposite to the skin-contact surface, that does not contact the skin of the wearer when the diaper is worn, and it does not oppose (face) the skin of the wearer.

In FIG. 1A, the absorbent body 2 is provided so as to bridge between the front around-torso member 3 and the back around-torso member 3. That is, the front portion 20, which is one end portion of the absorbent body 2 in the longitudinal direction Y, is joined (attached) to the front around-torso member 3. On the other hand, the back portion 21, which is another end portion of the absorbent body 2 in the longitudinal direction Y, is joined (attached) to the back around-torso member 3.

The front and back around-torso members 3 respectively form a pair of front and back flaps F and F protruding in the girth direction X from the absorbent body 2, and the flaps F form a part of the front and back around-torso portions. That is, as shown in FIG. 1A, the flaps F protrude in the girth direction X beyond the crotch portion 22, and are extending in the girth direction X from the opposite side edges E1 of the absorbent body 2 (the crotch portion 22).

The front and back around-torso members 3 are provided by cutting off a continuous laminate L (see FIG. 3A), which is described later.

As clearly shown in FIG. 2, each around-torso member 3 is made of a laminate including an elastic member 30, a first sheet 31, and a second sheet 32, layered on one another.

The first sheet 31 and a pair of second sheets 32 are formed by an air-permeable non-woven fabric. The first sheet 31 continuously extends in the girth direction X from the front torso or the back torso of the wearer to the opposite side portions. On the other hand, the pair of second sheets 32 and 32 are layered on the first sheet and spaced apart from each other in the girth direction X so that they are not provided in the front torso and the back torso but are placed in the opposite side portions.

The elastic member 30 is sandwiched between the first sheet 31 and the second sheets 32, and is stretchable in the girth direction X. The elastic member 30, the second sheets 32 and the first sheet 31 are layered on one another in the areas of the front and back flaps F as clearly shown in FIG. 1B. Thus, the flap F has three layers.

The elastic member 30 is cut off in front and back torso portions 34 between the pair of second sheets 32 and 32 spaced apart from each other in the girth direction X. That is, as shown in FIG. 1B, the first sheet 31 and the back sheet 27 are laminated with each other in a central part between the pair of second sheets 32 and 32 without sandwiching the elastic member 30 therebetween. Thus, the contractile force of the elastic member 30 is not exerted in the front and back torso portions 34 between the pair of second sheets 32 and 32.

As shown in FIG. 1A, with the present embodiment, one end portion 30e of the cut elastic member 30 protrudes from the second sheet 32 toward the front and back torso portions 34.

The elastic member 30 is for fitting the around-torso members 3 to the wearer. The elastic member 30 may be, for example, a plurality of rubber threads, rubber tapes, or a thread-shaped or a band-shaped material including a thermoplastic resin (e.g. hot-melt adhesive), or the like.

Where rubber threads are employed as the elastic member 30, an adhesive may be applied not over the entire surface of the first sheet 31 and the second sheets 32, but may be applied only on first and second end portions 32A, 32B of each second sheet 32 of FIG. 1B in the girth direction X, and the elastic member 30 may be sandwiched between (and joined to) the first sheet 31 and the second sheet 32 in the first joining portion 32A and 32B, thereby forming the laminate. The first joining portions 32A and 32B extend in the longitudinal direction Y, and are spaced apart from each other in the girth direction X. One end portion 30e of the cut elastic member 30 protrudes from the first joining portion 32A toward the center of the torso portion 34 in the girth direction X. Note that parts joined with adhesive are shown by a number of dots in Figures.

In addition to the joining with adhesive, the first sheet 31 and the second sheet 32 may be partially welded and joined with each other at second joining portions 42, as shown in a lot of small circles of FIG. 1A or a lot of small x marks of FIG. 1C. In this embodiment, each flap F has a structure in which the first sheet 31 and the second sheet 32 are intermittently joined with each other at a plurality of second joining portions 42, between adjacent elastic members 30, along an stretching (extension) direction X of each of the elastic members 30.

That is, in this case, the first sheet 31 may be welded to the second sheet 32 in only a part of the first sheet 31, as shown in xxx of FIG. 1C, which shows the welded parts.

In FIG. 1A, the absorbent body 2 is placed to extend between the front torso portion 34 and the back torso portion 34, where the second sheets 32 are not placed. In this embodiment, the absorbent body 2 is placed so as to cover (overlap with) at least a part of the first end portions 32A, 32A of the pair of second sheets 32 and 32. That is, as shown in FIG. 1B, the first sheet 31, the elastic members 30, the second sheet 32 and the back sheet 27 are laminated with one another in at least a part of the first end portion 32A of the second sheet 32.

The absorbent body 2 may include an around-leg portion where the absorbent body 2 is necked (constricted) in conformity with the legs of the wearer. The around-leg portion or a portion of the around-torso member 3 that is continuous with the around-leg portion may be provided with another elastic member formed by rubber threads, or the like, for example, so as to conform to the legs of the wearer.

Where the worn article is a diaper, a male touch fastener (not shown) may be secured to the skin-contact surface of the back around-torso member 3. On the other hand, a female touch fastener may be secured to the non-skin-contact surface of the front around-torso member 3.

Note that a tape material with a fastening agent applied thereon may be used instead of the male touch fastener, in which case the front around-torso member 3, or the like, needs to be provided with a surface on which the fastening agent adheres easily.

Where the worn article is pants-shaped, the end portion in the girth direction X of the front flap F and that of the back flap F may be welded to each other.

Next, a method for manufacturing the present worn article will be described with reference to FIG. 3.

A continuous sheet W1 of FIG. 3A to be the first sheet 31 of FIG. 2 is continuous in a carrying direction X along the girth direction X and is carried in the carrying direction X. During carrying the sheet W1, an adhesive C is applied by a coating applicator on portions corresponding to the first joining portions 32A and 32C of the continuous sheet W1. Note that the continuous sheet W1 and the discontinuous sheet W2 are both formed by an air-permeable non-woven fabric.

On the other hand, a plurality of continuous elastic members F3 of FIG. 3A to be the plurality of elastic members 30 of FIG. 2 are placed on the continuous sheet W1 while they are stretched. Each of the continuous elastic members F3 is continuous in the carrying direction X of the continuous sheet W1.

At the same time, a plurality of discontinuous sheets W2 of FIG. 3A are placed on the continuous sheet W1 intermittently and successively in the carrying direction X1. The discontinuous sheet W2 is placed so that the opposite side edges of the sheet W2 in the carrying direction X are overlapped with (superimposed on) the first joining portions 32A whereas the central portion of the sheet W2 is superimposed on (overlapped with) the first joining portion 32C. Thus, the continuous elastic member F3 is sandwiched between the discontinuous sheet W2 and the continuous sheet W1, thereby forming the continuous laminate L which is described later. The discontinuous sheet W2 becomes the second sheets 32 after being cut into two as shown in FIG. 3B.

As shown in FIG. 3A, when the continuous sheet W1, the continuous elastic members F3, and the discontinuous sheet W2 are sandwiched between nip rolls (not shown) and laminated with one another, the continuous sheet W1, the discontinuous sheet W2, and the continuous elastic members F3 are joined with one another with the adhesive C in the first joining portions 32A and 32C where the adhesive C are applied. That is, in the first joining step, the continuous sheet W1, the discontinuous sheet W2, and the continuous elastic members F3 are joined to one another, in an area where the discontinuous sheet W2 is placed, intermittently in the carrying direction X on the plurality of the first joining portions 32A and 32C extending in a width direction Y crossing the carrying direction X. The first joining portions 32A and 32C transversely cross a continuous laminate L.

In the first joining step, the first joining portions are formed in the opposite (both) ends 32A of the non-continuous sheet W2 and the central portion 32C. The central portion 32C is spaced apart from the opposite ends 32A and in between the opposite end portions 32A. The joining step may be achieved by joining the continuous sheet W1 and the discontinuous sheet W2 with each other by heat-sealing or ultrasonically sealing. A width of the first joining portion in the carrying direction X in the central portion 32C is larger than a width of the first joining portion in the carrying direction X in the opposite portions 32A.

Thereafter, the continuous laminate L is supplied onto a cutter (not shown), and the continuous elastic member F3 is cut between the intermittently-placed adjacent discontinuous sheets W2 and W2. Through this cutting, the contractile force from the continuous elastic member F3 is removed, while producing a plurality of discontinuous elastic members 30 in the carrying direction X.

Through the cutting, the opposite ends of the elastic member 30 will be exposed from the ends of the discontinuous sheet W2.

Note that the method for cutting the continuous elastic member F3 on the continuous sheet W1 is disclosed for example in U.S. Pat. No. 7,438,779 B2, the contents of which are herein incorporated by reference in its entirety.

In the second joining step, the continuous sheet W1 and the discontinuous sheet W2 may be intermittently joined together, by the plural second joining portions 42 along a stretching direction X of the elastic member F3, between the plurality of the first joining portions 32A, 32C in the area where the discontinuous sheet W2 is placed. In this embodiment, the second joining step may be carried out so that the plurality of second joining portions 42 is formed between the two adjacent elastic members 30 and the second joining portions 42 are formed so as to align in the stretching direction X and in the width direction Y.

Note that although FIG. 3A only shows one continuous laminate L for the sake of simplicity, a pair of continuous laminates L and L parallel to each other may actually be produced as shown in FIG. 3B.

The pair of continuous laminates L and L of FIG. 3B are supplied into between nip rolls (not shown). On the other hand, the absorbent bodies 2 are intermittently supplied, as shown in FIG. 3B, into between the nip rolls. The end portions 20 and 21 of each absorbent body 2 in the longitudinal direction Y are successively placed on the front and back portions 34 and 34 of the continuous sheets W1 (i.e., between the discontinuous sheets W2 adjacent with each other in the carrying direction X) with the absorbent bodies 2 bridged between the continuous sheets W1.

After the bridging, the continuous laminate L is cut along a virtual cut line extending in the width direction Y in the central portion 32C between the adjacent absorbent bodies 2 and 2 so as to obtain individual worn articles 1. That is, the continuous sheet W1, the elastic member 30 and the discontinuous sheet W2 are cut along a virtual cut line extending in the width direction Y perpendicular to the carrying direction X1. As a result, the central portion 32C becomes a pair of second end portions 32B.

Note that after the cutting, the individual worn articles 1 are each folded in two at the absorbent body 2, thereby producing a diaper- or pants-type worn article 1.

FIGS. 4A to 5B show Embodiment 2. Embodiment 2 will now be described primarily with respect to the differences from Embodiment 1.

Figure 4A:
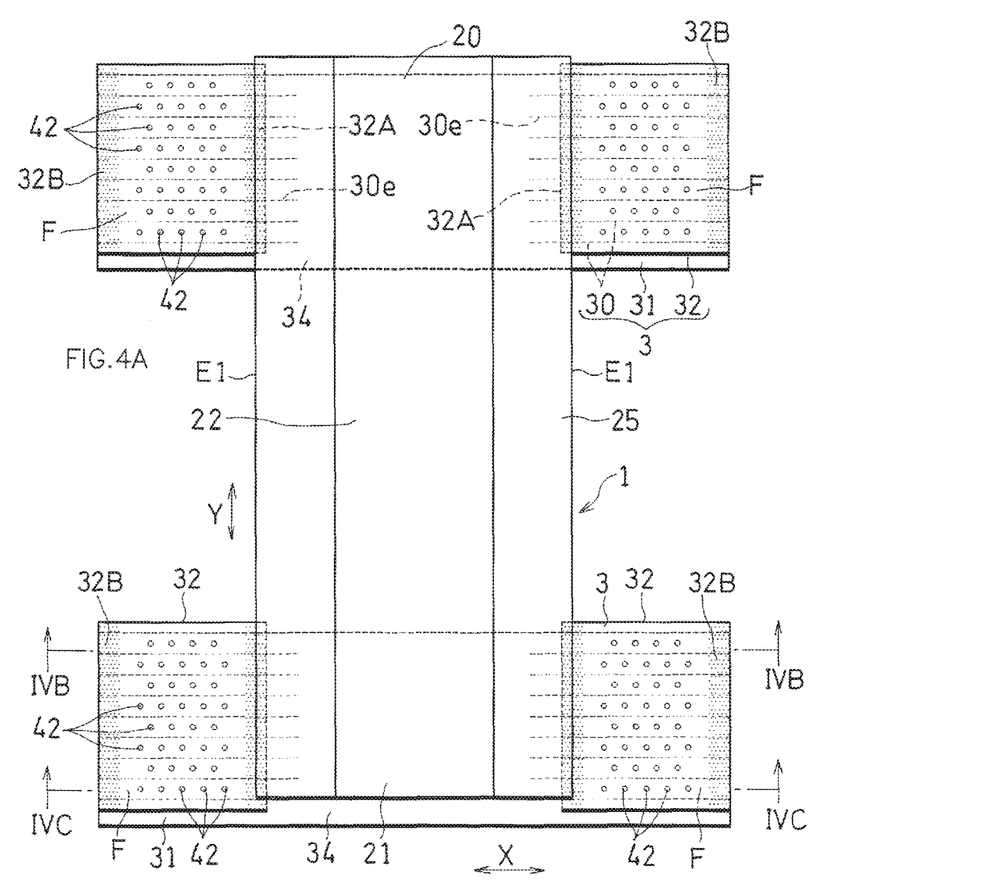
FIG. 4A is a schematic exploded perspective view showing the article unfolded as seen in a diagonally forward direction.
Figure 4B:
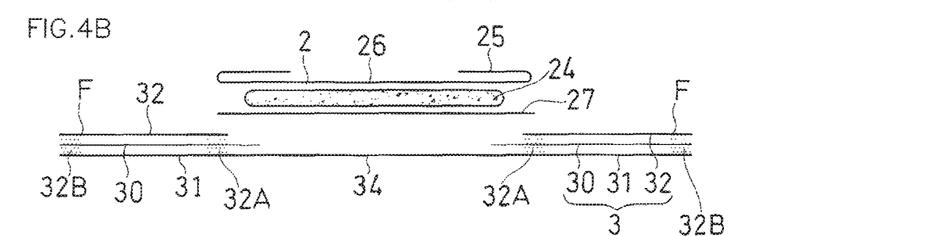
FIGS. 4B and 4C show respectively a cross-sectional view along IVB-IVB of FIG. 4A and a cross-sectional view along IVC-IVC of FIG. 4A.
Figure 4C:
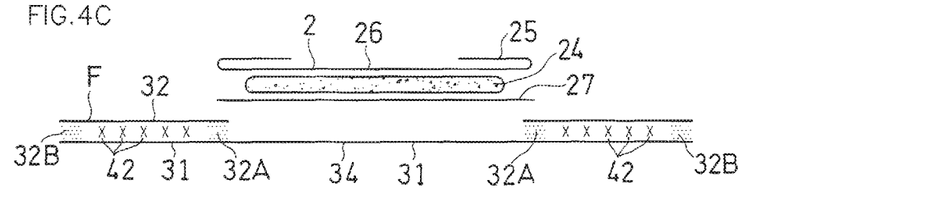
Figure 5A:
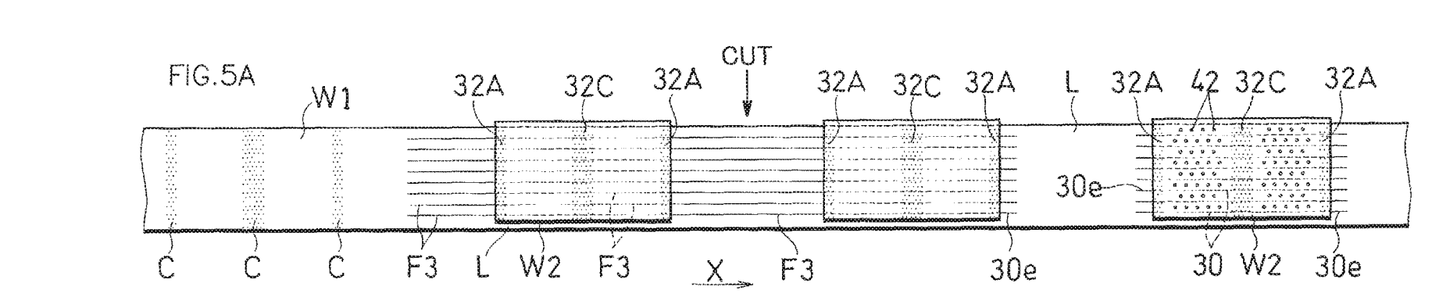
FIGS. 5A and 5B are each a schematic exploded perspective view showing an example of a method for manufacturing the worn article.
Figure 5B:
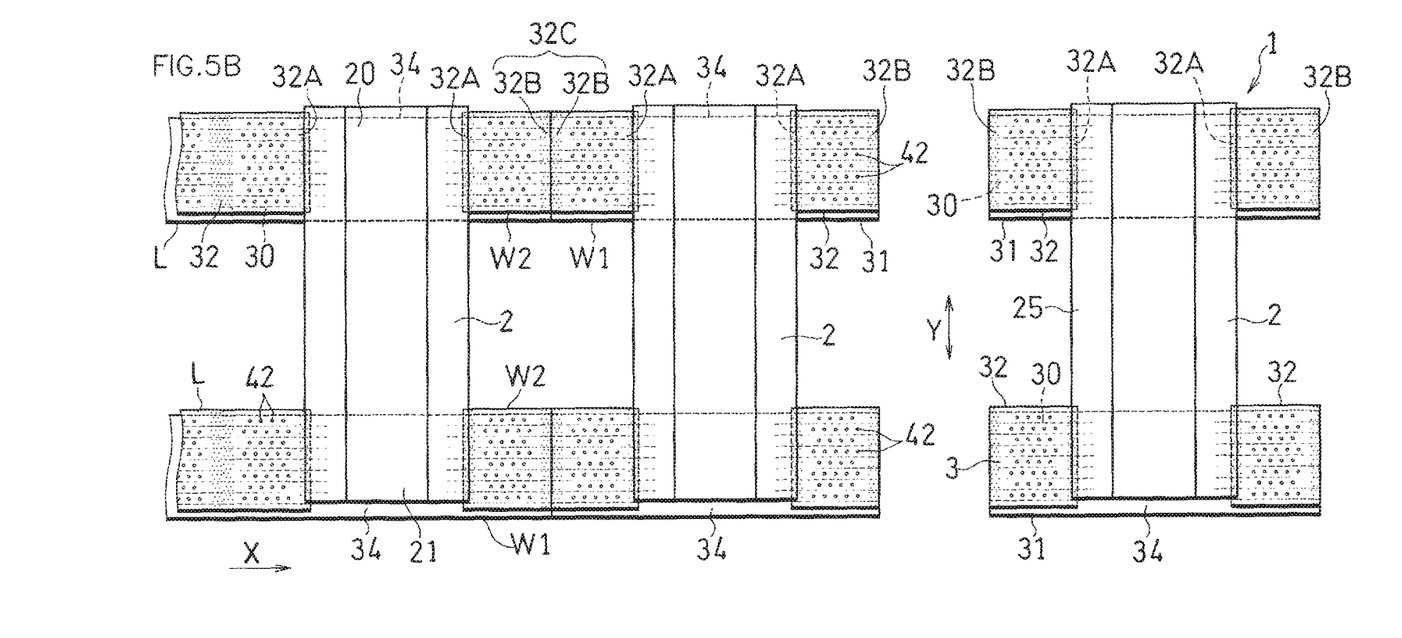

As shown in FIG. 4A, in this embodiment 2, the second joining portions 42 are arranged so that they are displaced in relation to one another (they are staggered).

The structure of the worn article 1 of the present embodiment and the method for manufacturing the same are otherwise similar to Embodiment 1, and like elements are denoted by like reference numerals and will not be further described or illustrated hereinbelow.

FIGS. 6A to 7B show Embodiment 3. Embodiment 3 will now be described primarily with respect to the differences from Embodiment 1.

Figure 6A:
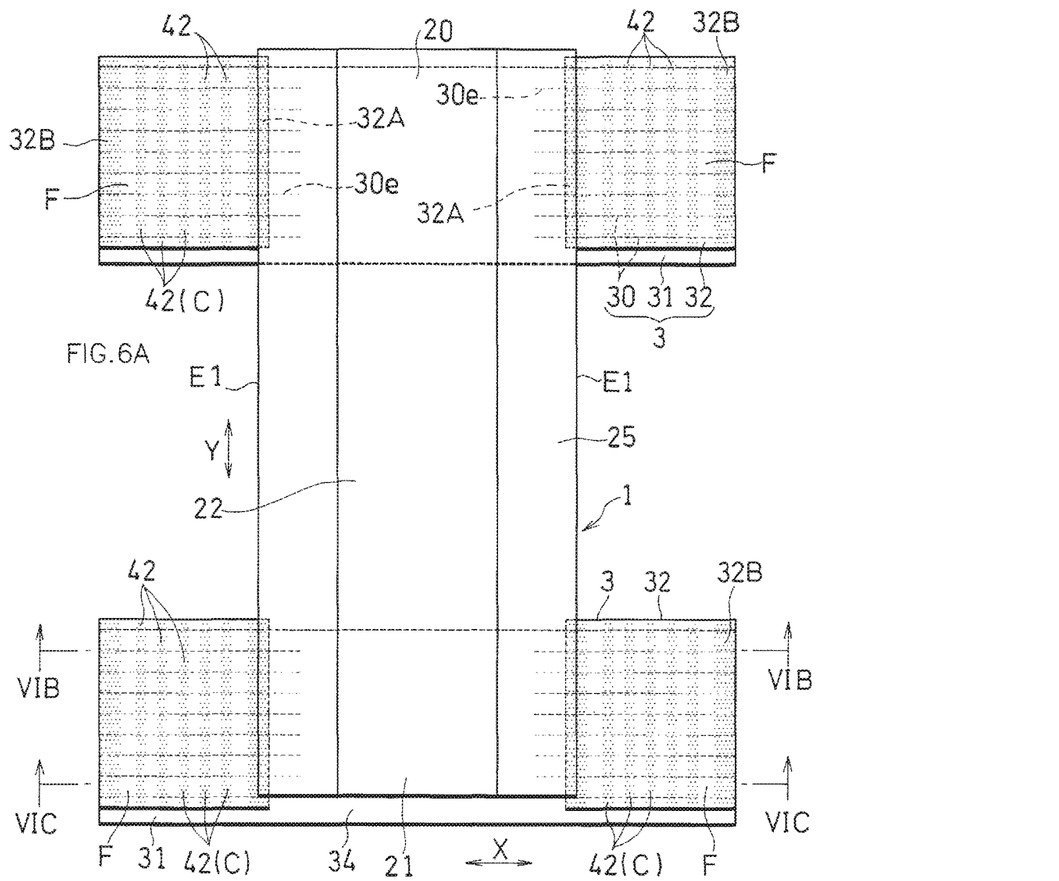
FIG. 6A is a schematic exploded perspective view showing the article unfolded as seen in a diagonally forward direction.
Figure 6B:
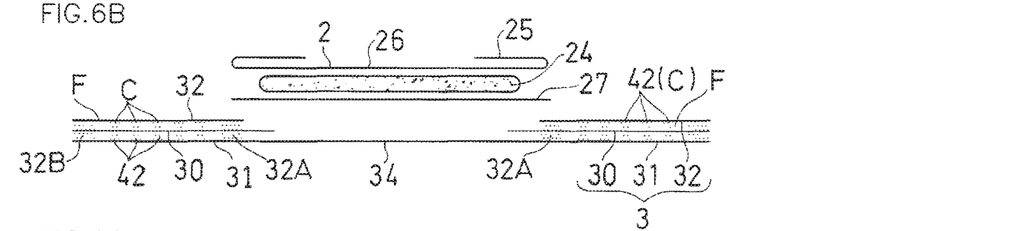
FIGS. 6B and 6C show respectively a cross-sectional view along VIB-VIB of FIG. 6A and a cross-sectional view along VIC-VIC of FIG. 6A.
Figure 6C:
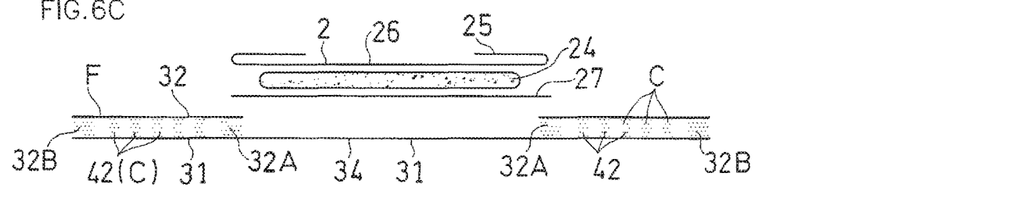

As shown in FIG. 6A, in the present embodiment 3, the second joining portions 42 are formed in thin stripes extending in the width direction Y. The stripe-shaped second joining portions 42 are provided so as to transversely cross the first and second sheets 31 and 32 in the width (longitudinal) direction Y. In the second joining portion 42, the continuous sheet W1, the discontinuous sheet W2, and the continuous elastic members F3 of FIG. 7A are joined together by the adhesive C (e.g., hot-melt adhesive), as shown by the many dots in FIGS. 6B and 6C, in order to be less likely to impair elasticity of the elastic members 30.

Figure 7A:
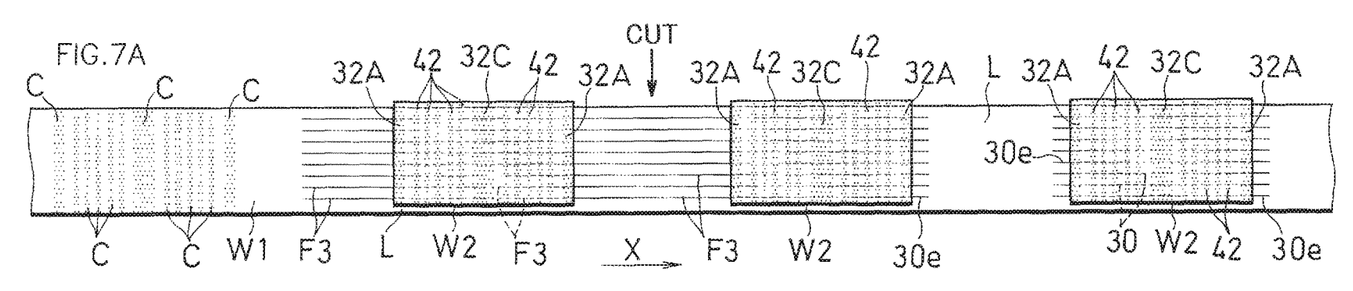
FIGS. 7A and 7B are each a schematic exploded perspective view showing an example of a method for manufacturing the worn article.
Figure 7B:
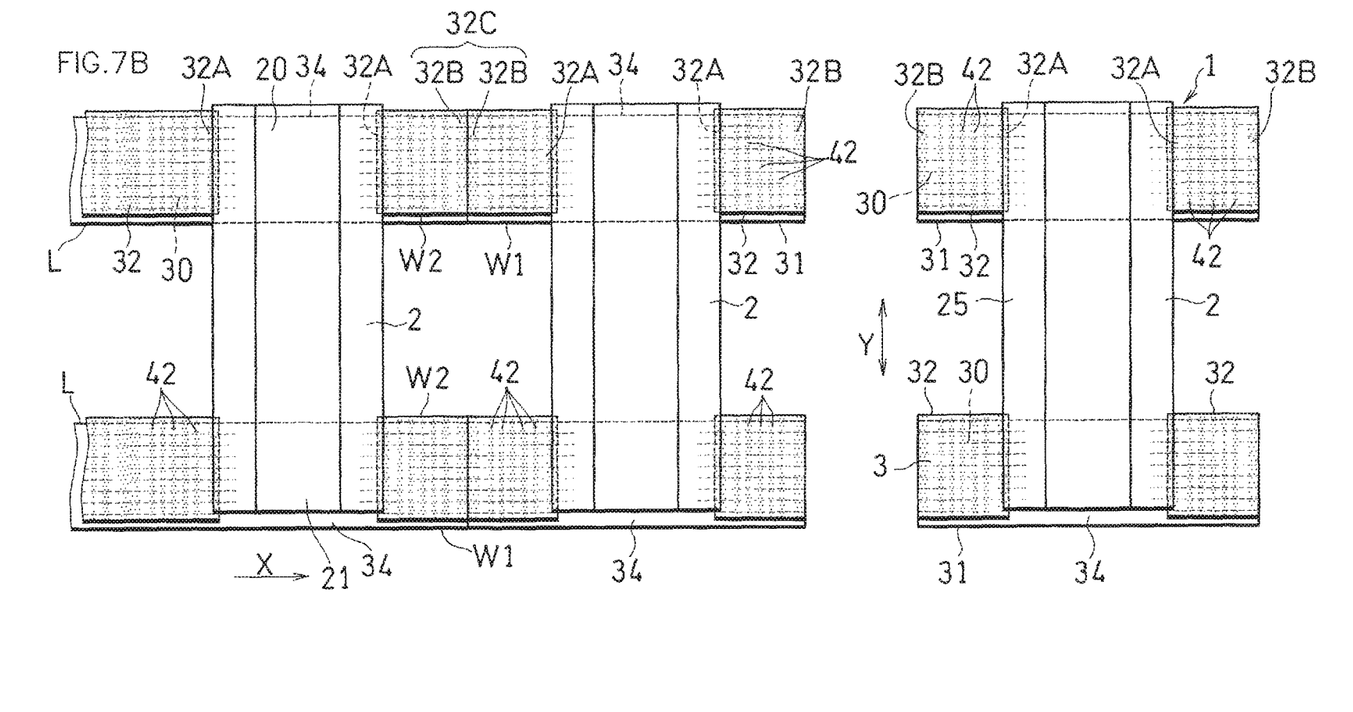

As shown in FIG. 7A, in this embodiment, the adhesive C are previously applied not only on the first joining portions 32A and 32C but also on portions corresponding to the second joining portions 42. After the application of the adhesive, the continuous elastic members F3 and the discontinuous sheet W2 are placed.

The structure of the worn article 1 of the present embodiment and the method for manufacturing the same are otherwise similar to Embodiment 1, and like elements are denoted by like reference numerals and will not be further described or illustrated hereinbelow.

FIGS. 8A to 9B show Embodiment 4. Embodiment 4 will now be described primarily with respect to the differences from Embodiment 1.

Figure 8A:
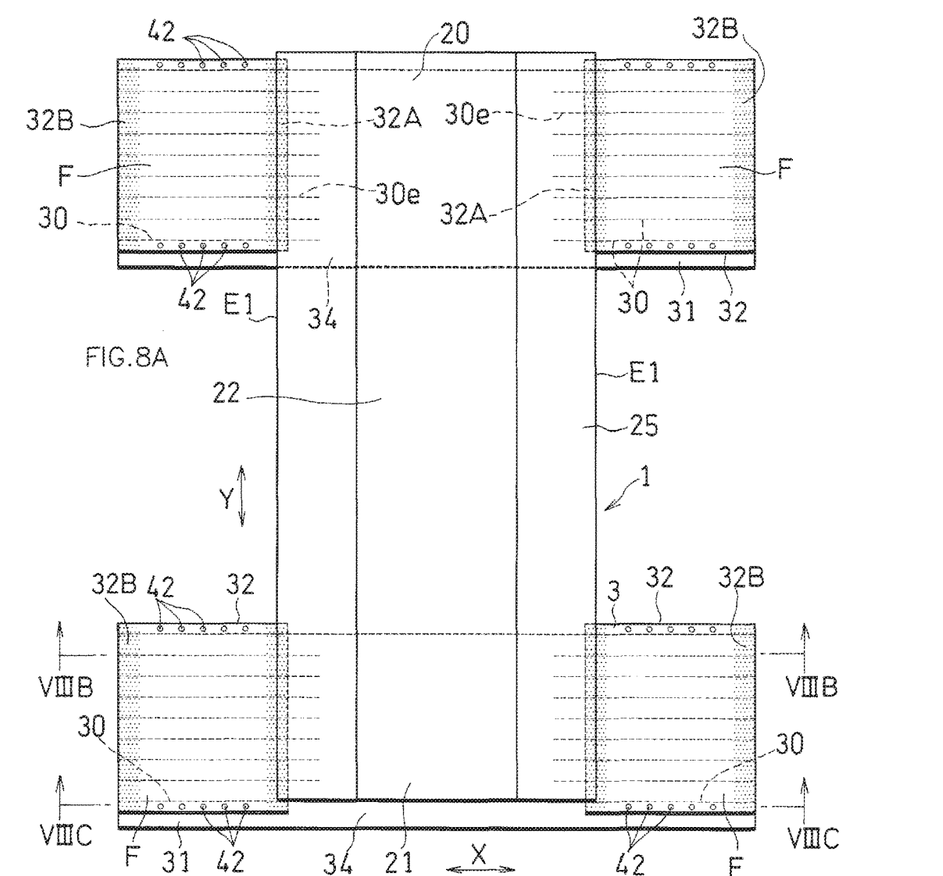
FIG. 8A is a schematic exploded perspective view showing the article unfolded as seen in a diagonally forward direction.
Figure 8B:
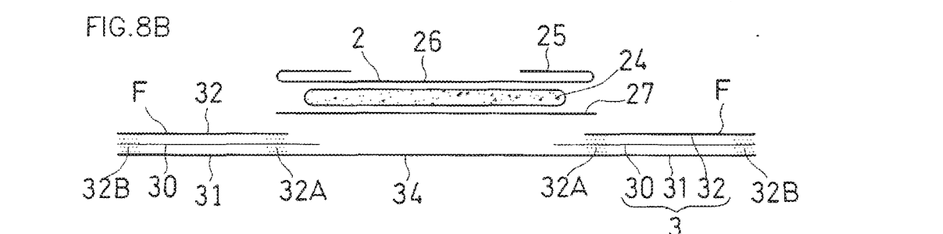
FIGS. 8B and 8C show respectively a cross-sectional view along VIIIB-VIIIB of FIG. 8A and a cross-sectional view along VIIIC-VIIIC of FIG. 8A.
Figure 8C:
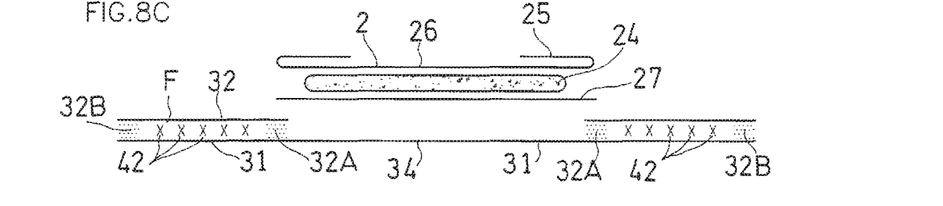

In the present embodiment 4, a plurality of the second joining portions 42 of FIG. 8A are formed so as to be arranged along the opposite (both) side edges of the second sheet 32 in the width (longitudinal) direction Y (i.e., arranged in an area closer to the edge than the elastic member 30 that is closest to the edge among the elastic members 30). That is, the plurality of second joining portions 42 are intermittently placed along the carrying direction X between the side edge of the second sheet 32 and the elastic member 30 that is closest to the side edge among the elastic members 30.

Figure 9A:
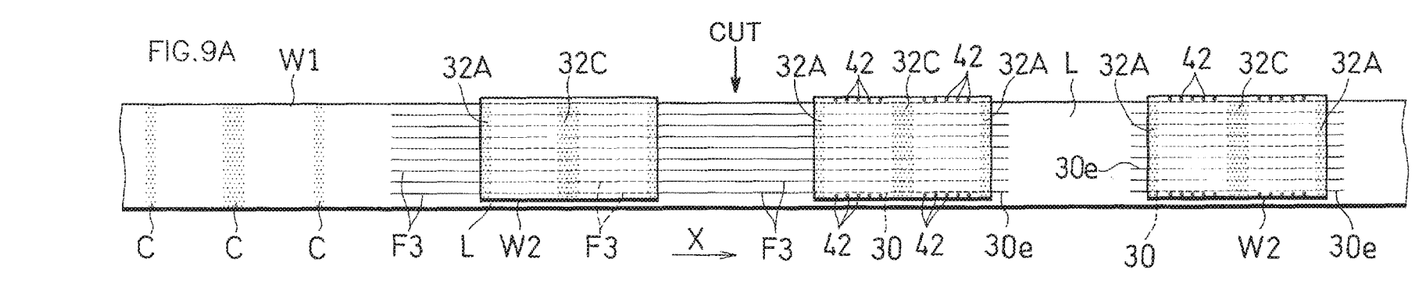
FIGS. 9A and 9B are each a schematic exploded perspective view showing an example of a method for manufacturing the worn article.
Figure 9B:
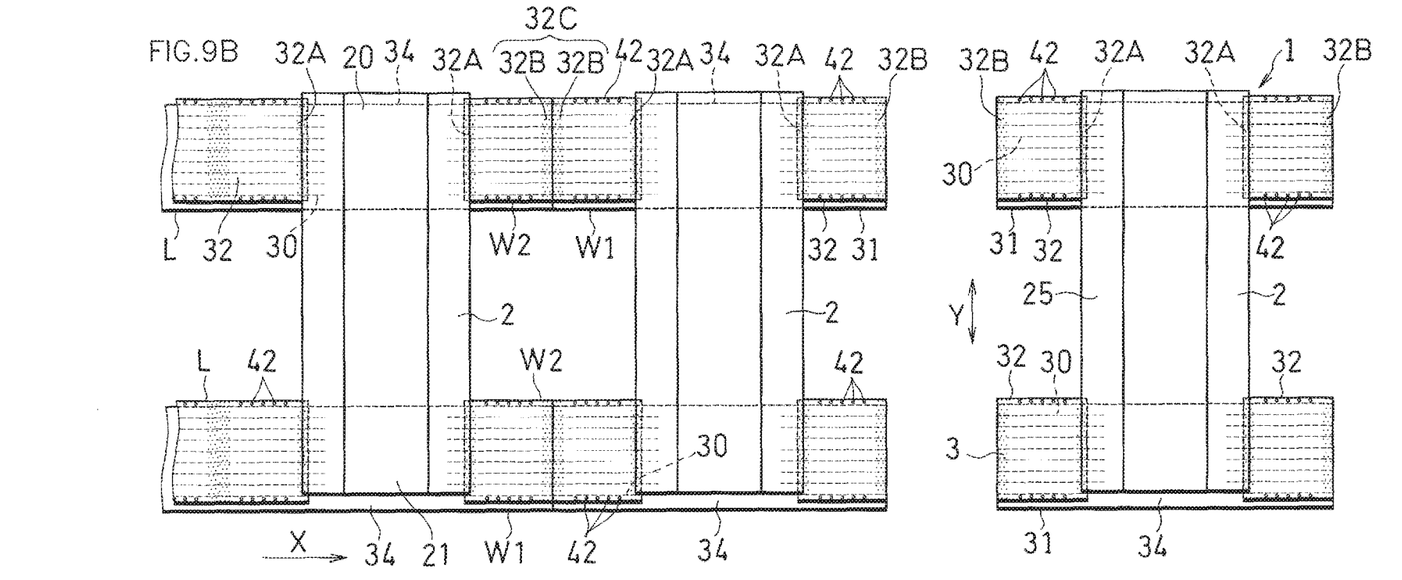

In the embodiment 4, the second joining portions 42 are formed before cutting the continuous elastic members F3 of FIG. 9A. That is, the second joining step is carried out by forming the plurality of second joining portions 42 along the opposite side edges of the discontinuous sheet W2 in the width direction Y, for example, soon after the first joining step.

The structure of the worn article 1 of the present embodiment and the method for manufacturing the same are otherwise similar to Embodiment 1, and like elements are denoted by like reference numerals and will not be further described or illustrated hereinbelow.

While preferred embodiments have been described above with reference to the drawings, various obvious changes and modifications will readily occur to those skilled in the art upon reading the present specification.

For example, a worn article manufactured by the present manufacturing method may have a design pattern (drawing) thereon.

In addition, a worn article may be T-shaped diaper.

Furthermore, the second joining portions may not be provided.

Thus, such changes and modifications are deemed to fall within the scope of the present invention, which is defined by the appended claims.

INDUSTRIAL APPLICABILITY

The present invention is applicable to a diaper-shaped or pants-shaped disposable worn article, and a method for manufacturing the same.

REFERENCE SIGNS LIST

1: Worn article
2: Absorbent body (interior portion) 20: Front portion (end portion) 21: Back portion (end portion) 22: Crotch portion
24: Absorbent core 25: Cuff 26: Top sheet 27: Back sheet
3: Around-torso member (exterior portion) 3A: Exterior portion
30: Elastic member 30e: End portion 31: First sheet 32: Second sheet 32A: First end portion (First joining portion) 32B: Second end portion (First joining portion) 32C: Central portion (First joining portion) 34: Front and back torso portions
42: Second joining portion
C: Adhesive F: Front flap L: Continuous laminate
X: Girth direction (Carrying direction) Y: Longitudinal direction (width direction)
F3: Continuous elastic member
W1: Continuous sheet W2: Discontinuous sheet

The invention claimed is:
1. A method for manufacturing a disposable worn article comprising the steps of:
carrying a continuous sheet that is continuous in a carrying direction;
placing a plurality of continuous elastic members, which are continuous in the carrying direction of the continuous sheet, on the continuous sheet with each of the continuous elastic members stretched;
placing a plurality of discontinuous sheets, each of which has a predetermined length, on the continuous sheet intermittently and successively in the carrying direction so that the continuous elastic members are sandwiched between the discontinuous sheets and the continuous sheet; and
carrying out a first joining step in which, in an area where each of the discontinuous sheets is placed, the continuous sheet, each of the discontinuous sheets, and the continuous elastic members are joined to one another, intermittently in the carrying direction, along a plurality of first joining portions extending in a width direction crossing the carrying direction the first joining portions extending across the continuous sheet, wherein
in the first joining step, the first joining portions are formed in opposite end portions of each of the discontinuous sheets in the carrying direction and in a central portion of each of the discontinuous sheets, the central portion being spaced apart from the opposite end portions and between the opposite end portions,
the first joining portions are formed only in the opposite end portions and the central portion of each of the discontinuous sheets, and
the continuous elastic members are joined to the continuous sheet and each of the discontinuous sheets only in the opposite end portions and the central portion of each of the discontinuous sheets,
the method further comprises the steps of:
cutting the continuous elastic members between two discontinuous sheets of the plurality of discontinuous sheets, the two discontinuous sheets being adjacent to each other in the carrying direction,
the continuous elastic members that are cut in the step of cutting shrinking and shortening toward the discontinuous sheets, thereby intermittently producing groups of discontinuous elastic members in the carrying direction;
carrying out a second joining step in which, between the plurality of first joining portions in the area where each of the discontinuous sheets is placed, the continuous sheet and each of the discontinuous sheets are intermittently joined to each other, along a stretching direction of the discontinuous elastic members, on a plurality of second joining portions,
the second joining step is carried out so that the plurality of second joining portions are formed only between two discontinuous elastic members of each of the groups of discontinuous elastic members, the two discontinuous elastic members being adjacent to each other in the width direction;
successively placing one end portion, in the carrying direction, of each of a plurality of absorbent bodies on the continuous sheet between two discontinuous sheets of the discontinuous sheets, adjacent to each other in the carrying direction, and between two groups of the groups of discontinuous elastic members, adjacent to each other in the carrying direction;

cutting the continuous sheet and each of the discontinuous sheets in the central portion along the width direction crossing the carrying direction in order to obtain individual worn articles.

2. The manufacturing method according to claim 1, wherein
in the first joining step, the continuous sheet, each of the discontinuous sheets, and the continuous elastic members are joined to one another by an adhesive to intermittently form the first joining portions, and
in the second joining step, the continuous sheet and each of the discontinuous sheets are partially welded and joined with each other at the second joining portions.

* * * * *